United States Patent [19]

Dall'Asta

[11] Patent Number: 4,485,248

[45] Date of Patent: Nov. 27, 1984

[54] PROCESS FOR PRODUCING 2,4-DIAMINO-(3,5-DIMETHOXY-4-METHOXYETHOXY-BENZYL)-PYRIMIDINE

[75] Inventor: Leone Dall'Asta, Pavia, Italy

[73] Assignee: Proter S.p.A., Milan, Italy

[21] Appl. No.: 399,343

[22] Filed: Jul. 19, 1982

[30] Foreign Application Priority Data

Aug. 11, 1981 [IT] Italy ............................. 23462 A/81

[51] Int. Cl.$^3$ ............................................ C07D 239/49
[52] U.S. Cl. ....................................... 544/325; 544/320
[58] Field of Search ...................................... 544/325

[56] References Cited

U.S. PATENT DOCUMENTS

| | | | |
|---|---|---|---|
| 3,485,840 | 12/1969 | Hoffer | 544/325 |
| 4,116,958 | 9/1978 | Stuart et al. | 544/325 |
| 4,143,227 | 3/1979 | Rosen | 544/325 |
| 4,203,980 | 5/1980 | Kompis et al. | 544/325 |
| 4,255,574 | 3/1981 | Rosen | 544/325 |
| 4,258,045 | 3/1981 | Poe et al. | 544/325 |

Primary Examiner—Glennon H. Hollrah
Assistant Examiner—James H. Turnipseed
Attorney, Agent, or Firm—Stevens, Davis, Miller & Mosher

[57] ABSTRACT

A process for preparing Tetroxoprim starting from 3,5-dimethoxy-4-methoxyethoxy-benzaldehyde and 2,4-diamino-6-hydroxy-pyrimidine, by successive hydrogenation, halogenation and hydrogenolysis of the 2,4-diamino-6-oxo-5-(3,5-dimethoxy-4-methoxyethoxy-benzylidene)-pyrimidine obtained in the initial reaction.

8 Claims, No Drawings

PROCESS FOR PRODUCING 2,4-DIAMINO-(3,5-DIMETHOXY-4-METHOXYETHOXY-BENZYL)-PYRIMIDINE

This invention relates to a new process for producing 2,4-diamino-(3,5-dimethoxy-4-methoxyethoxy-benzyl)-pyrimidine of formula:

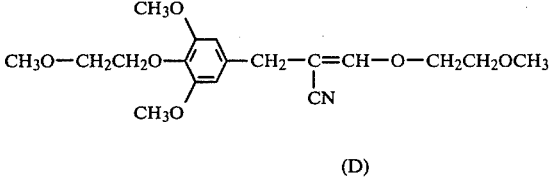

(I)

known by the common name of Tetroxoprim.

Tetroxoprim is a product which has been synthesised for some years (Belgian Pat. No. 812,375), and is similar to Trimethoprim, from which it differs chemically only in that it comprises a methoxyethoxy group instead of a simple methoxy group in position 4 on the benzyl.

However, from the point of view of antibacterial activity, Tetroxoprim has proved considerably superior to Trimethoprim, and has thus assumed an important position in the pharmaceutical industry, which requires ever-increasing quantities of it.

Of the numerous processes proposed for its preparation (Belgian Pat. No. 812,375), only one has proved economically significant and has found application on an industrial scale. Said process comprises essentially the following stages:

(a) reacting 3,5-dimethoxy-4-methoxyethoxy-benzaldehyde with β-methoxypropionitrile, in the presence of sodium methylate

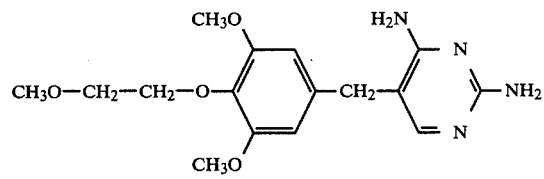

(B)

CH₃O—CH₂CH₂CN ⟶

$$CH_3O-CH_2CH_2O-\underset{CH_3O}{\underset{|}{C_6H_2}}-CH=C(CN)-CH_2-OCH_3$$

(C)

(b) transforming compound (C) into compound (D) by heating at 90° C. with methyl cellosolve and sodium $$CH_3O-CH_2CH_2O-\underset{CH_3O}{\underset{|}{C_6H_2}}-CH=C(CN)-CH_2OCH_3 \longrightarrow$$

-continued $$CH_3O-CH_2CH_2O-\underset{CH_3O}{\underset{|}{C_6H_2}}-CH_2-C(CN)=CH-O-CH_2CH_2OCH_3$$

(D)

(c) condensing compound (D) with guanidine at 140° C., again in the presence of methyl cellosolve and sodium $$(D) + H_2N-\underset{\|}{\overset{NH}{C}}-NH_2 \cdot HCl \longrightarrow$$

$$CH_3O-CH_2CH_2O-\underset{CH_3O}{\underset{|}{C_6H_2}}-CH_2-\text{pyrimidine}(NH_2)_2$$

By means of this process, the Tetroxoprim is obtained with an overall yield of 22% (Cronache Farmaceutiche No. 3, 1980).

A new process has now been found, and forms the subject matter of the present invention, which can be carried out on an industrial scale much more economically than the process of the known art, both because it uses raw materials which are all already available commercially, and because in contrast to the old process all the stages lead to crystalline intermediate products which can be easily isolated without the use of complicated and costly separation techniques.

In addition, the process according to the present invention gives very high overall yields which are always greater than 80%, in comparison with the 22% obtainable by the process of the known art.

The new process comprises the stages schematically indicated hereinafter, and is carried out under the stated operating conditions:

1. Reacting 3,5-dimethoxy-4-methoxyethoxy-benzaldehyde with 2,4-diamino-6-hydroxy-pyrimidine $$CH_3O-CH_2CH_2O-\underset{CH_3O}{\underset{|}{C_6H_2}}-CHO + \text{pyrimidine}(NH_2)_2(OH) \longrightarrow$$

(II)     (III)

$$CH_3O-CH_2CH_2O-\underset{CH_3O}{\underset{|}{C_6H_2}}-CH=\text{pyrimidinone}(NH_2)_2$$

(IV)

This reaction is carried out in solution in a reaction medium preferably chosen from the group consisting of water, aqueous ethanol, aqueous acetic acid, aqueous NaOH solution, methyl cellosolve, dimethylsulphoxide, ethylene glycol, dioxane or their mixtures.

The temperature is between 50° and 150° C.

The reaction time varies with temperature.

At 100° C., with a reaction time of 6–10 hours, the yield is practically quantitative.

2. Reducing compound (IV) with hydrogen under pressure, in the presence of a catalyst

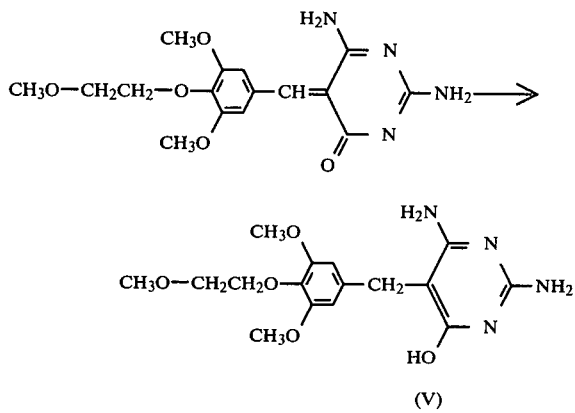

The hydrogenation is carried out in solution, preferably in a polar solvent generally mixed with between 5 and 50% of water, e.g. in a cellosolve/water mixture.

Best results are obtained by using Pd on carbon as catalyst, at a temperature of 50°–100° C., and with a hydrogen pressure of 1–8 atm.

Under optimum conditions, the yield is practically quantitative.

3. Halogenation of compound (V) by means of a suitable halogenation agent, with the formation of 2,4-diamono-6-halo-5-(3,5-dimethoxy-4-methoxyethoxy-benzyl)-pyrimidine

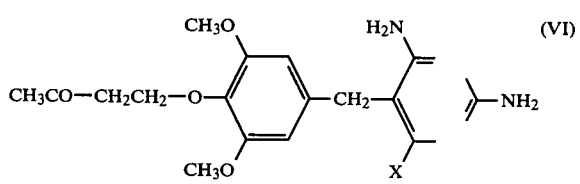

in which X is halogen, preferably Cl or Br.

The substitution of the hydroxyl by a halogen atom can be carried out using phosphorus oxychloride or oxybromide.

The reaction is carried out in solution, preferably using an excess of the actual halogenation agent as the solvent. Alternatively, hydrocarbon solvents or halogenated hydrocarbons can be used as diluents for the halogenation agent. Toluene can be conveniently used.

The reaction temperature lies between 100° and 120° C.

The reaction times vary with temperature.

If a phosphorus oxychloride at boiling point is used as the solvent and halogenation agent, the reaction is complete in about 4 hours.

The halogenated product yield is about 80%.

4. Hydrogenolysis of the halogen atom, with the formation of compound (I)

The hydrogenolysis can be carried out by various alternative methods.

According to a first preferred alternative, the hydrogenolysis is carried out in an acetic acid solution in the presence of sodium acetate, in an autoclave, under a hydrogen pressure of 1.5–2 atm., at ambient temperature, using Pd on carbon as the catalyst. The reaction is complete in 4–5 hours.

According to a further alternative, the hydrogenolysis is carried out in an acetic acid solution containing Zn powder, under reflux. Under these conditions, the reaction is complete in 15–24 hours.

In all cases, the product (I) is isolated from the acetic solution, with high purity and practically quantitative yields, by diluting with water, alkalising with an inorganic base, preferably ammonium hydroxide, and extracting with a suitable organic solvent such as chloroform or ethyl acetate.

The final products of the individual stages heretofore defined must be isolated before passing to the next stage. As already stated, the intermediate products are already very pure and crystalline, so that no purification is necessary before passing them to the next stage.

In order to facilitate reproduction of the new process according to the present invention and to clarify the operational details, one practical example is described hereinafter, which however must in no way be assumed to limit the scope of the invention.

In particular, purification of the intermediate products as described in the example has been carried out only for the purpose of identifying and characterising the products themselves, whereas on an industrial scale purification is absolutely unnecessary.

EXAMPLE (a)

2,4-diamino-6-oxo-5-(3,5-dimethoxy-4-methoxyethoxy-benzylidene)-pyrimidine (IV)

63 g of 2,4-diamino-6-hydroxy-pyrimidine (0.46 m) are dissolved in 500 ml of water, by heating to 100° C.

72.08 g of 3,5-dimethoxy-4-methoxyethoxy-benzaldehyde (0.30 m) are added in portions.

The reaction mixture is heated under stirring for 20 hours at 100° C. On termination of heating, about 200 ml of water are distilled off at atmospheric pressure.

The mixture is cooled to 25° C., filtered, the product washed with water and dried under vacuum at 40° C.

95 g (91%) of products of light yellow colour are obtained, with a M.P. of 266°–271° C. (decomposed).

Analysis: for $C_{16}H_{20}N_4O_5$ (M.W. 358.36), calc.: C 55.16%, H 5.79%, N 16.08%. found: C 54.88%, H 5.83%, H 15.97%.

The IR and NMR spectra agree with the assigned structure.

(b)

2,4-diamino-6-hydroxy-5-(3,5-dimethoxy-4-methoxyethoxybenzyl)-pyrimidine (V)

12 g of (IV) (0.034 m) are dissolved in a mixture of ethylene glycol monoethyl ether (208 ml) and water (45 ml).

1.750 g of 10% Pd/C are added to the solution, which is then hydrogenated at 3.5 atm. and 80° C. for 16 hours.

It is cooled, the catalyst is filtered off, and the filtrate is concentrated under reduced pressure at 60° C.

The residue is taken up in water (10 ml), and the solid product is collected in a Buchner funnel, then finally washed with cold water (+5° C.).

It is dried under vacuum at 40° C.

10.450 g (87.7%) of white product are obtained, with a M.P. of 192° C. (decomposed).

Analysis: for $C_{16}H_{22}N_4O_5$ (M.W. 350.38), calc.: C 54.84%, H 6.33%, N 15.99%. found: C 55.02%, H 6.38%, N 16.00%.

The IR and NMR spectra agree with the assigned structure.

(c)
2,4-diamino-6-chloro-5-(3,5-dimethoxy-4-methoxyethoxy-benzyl)-pyrimidine (VI)

270 ml of phosphorus oxychloride are added to 27 g of (V) (0.077 m), and the mixture is heated to 105°–110° C. for 4 hours.

After cooling to 25° C., the excess chlorinating agent is removed by distillation under reduced pressure at 35°–40° C.

The residue is treated with ice (100 g), and the acid solution obtained is neutralised with an aqueous ammonium hydroxide solution.

The gummy mass which separates is crystallised from a 70:30 (v/v) acetone/water mixture.

It is filtered through a Buchner funnel, and the product washed with cold water (5° C.). It is dried under vacuum at 40° C.

22.6 g (79.6%) of a slightly yellow product are obtained, with a M.P. of 180° C. (decomposed).

Analysis: for $C_{16}H_{21}ClN_4O_4$ (M.W. 368.82), calc.: C 52.10%, H 5.74%, N 15.19%, Cl 9.61%. found: C 52.28%, H 5.65%, N 14.99%, Cl 9.60%.

(d)
2,4-diamino-6-(3,5-dimethoxy-4-methoxyethoxy-benzyl)-pyrimidine (I)

36.8 g of (VI) (0.1 m) are suspended in 810 ml of glacial acetic acid, and 27.07 g of anhydrous sodium acetate (0.33 m) and 3.5 g of 10% Pd/C are added to the suspension.

The mixture is hydrogenated at atmospheric pressure and 20°–25° C. under strong stirring.

After about 1 hour, the theoretical quantity of $H_2$ has been completely absorbed. The catalyst is filtered off, the filtrate is diluted with 1350 ml of water, and its pH is adjusted to 8.5 with a 30% $NH_4OH$ solution.

The solid product which separates is extracted with 1000+500 ml of chloroform. The organic phase is then separated, washed with water, dried with anhydrous sodium sulphate, filtered and concentrated under reduced pressure at 40° C.

The residue is crystallised from ethanol (160 ml).

31.7 g (95%) of white product are obtained, with a M.P. of 154°–156° C.

Analysis: for $C_{16}H_{22}N_4O_4$ (M.W. 334.38), calc.: C 57.47%, H 6.63%, N 16.75%. found: C 56.98%, H 6.62%, N 16.80%.

NMR spectrum ($CDCl_3$/TMS): 3.4 ppm (s, 3H, Ar—O—$CH_2$—$CH_2$—$OCH_3$), 3.6–3.7 (m. 4H, Ar—$CH_2$—, Ar—$OCH_2$—) 3.8 (s, 6H, $(OCH_3)_2Ar$), 3.9–4.15 (m, 2H, —$CH_2$—O—Ar), 4.59 (s, 2H,4—$NH_2$), 4.75 (s, 2H,2—$NH_2$), 6.40 (s, 2H, relative to the benzene nucleus), 7.80 (s, 1H, relative to the pyrimidine nucleus).

IR spectrum (KBr): —$NH_2$ (3100–3500 cm$^{-1}$); —CH-aliph. (2800–3000 cm$^{-1}$); heterocyclic and aromatic nucleus (1630, 1615, 1595 cm$^{-1}$).

I claim:

1. A process for producing 2,4-diamino-(3,5-dimethoxy-4-methoxyethoxy-benzyl)-pyrimidine of formula:

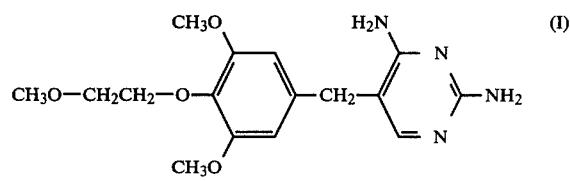

characterised in that:
(1) 3,5-dimethoxy-4-methoxyethoxy-benzaldehyde is reacted with 2,4-diamino-6-hydroxy-pyrimidine;
(2) the 2,4-diamino-6-oxo-5-(3,5-dimethoxy-4-methoxyethoxy-benzylidene)-pyrimidine thus obtained is reduced by hydrogen under pressure;
(3) the 2,4-diamino-6-hydroxy-5-(3,5-dimethoxy-4-methoxyethoxy-benzyl)-pyrimidine is halogenated by normal halogenation agents;
(4) the 2,4-diamino-6-halo-5-(3,5-dimethoxy-4-methoxyethoxy-benzyl)-pyrimidine is dehalogenated by means of hydrogenolysis.

2. A process as claimed in claim 1, wherein stage (1) is carried out in solution, at a temperature of between 50° and 150° C.

3. A process as claimed in claim 2, wherein the reaction solvent is chosen from the group consisting of water, aqueous ethanol, aqueous acetic acid, aqueous NaOH, methyl cellosolve, dimethylsulphoxide, ethylene glycol, dioxane and their mixtures.

4. A process as claimed in claim 1, wherein stage (2) is carried out in a solution comprising a polar solvent mixed with a water quantity of between 5 and 50%, in the presence of Pd on carbon as catalyst, at a temperature of between 50° and 100° C.

5. A process as claimed in claim 1, wherein stage (3) is carried out by means of a phosphorus oxyhalide, at a temperature of between 100° and 120° C.

6. A process as claimed in claim 1, wherein the phosphorus oxyhalide is diluted with an inert organic solvent.

7. A process as claimed in claim 1, wherein stage (4) is carried out by means of hydrogen in the presence of Pd on carbon as catalyst, at a pressure of 1.5–2 atm., at ambient temperature, in the presence of acetic acid and sodium acetate.

8. A process as claimed in claim 1, wherein stage (4) is carried out by means of Zn and acetic acid, at the mixture reflux temperature.

* * * * *